United States Patent
Sinha (12)

(10) Patent No.: US 6,379,669 B1
(45) Date of Patent: *Apr. 30, 2002

(54) TARGETING OF ORGANS BY IMMUNOCONJUGATES

(76) Inventor: Akhouri A. Sinha, 3254 48th Ave., Minneapolis, MN (US) 55406

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/691,565

(22) Filed: Aug. 2, 1996

Related U.S. Application Data

(60) Provisional application No. 60/001,892, filed on Aug. 4, 1995.

(51) Int. Cl.⁷ ............................................. A61K 39/395
(52) U.S. Cl. ................. 424/178.1; 424/179.1; 424/181.1; 424/183.1
(58) Field of Search .......................... 424/183.1, 236.1, 424/178.1, 179.1, 181.1; 530/391.1, 391.3, 391.7

(56) References Cited

U.S. PATENT DOCUMENTS

| | | | |
|---|---|---|---|
| 5,116,615 A | | 5/1992 | Gokcen et al. |
| 5,153,118 A | | 10/1992 | Wright, Jr. et al. |
| 5,227,471 A | | 7/1993 | Wright, Jr. |
| 5,489,525 A | * | 2/1996 | Pastan |
| 5,538,866 A | * | 7/1996 | Israeli et al. ............... 435/69.3 |
| 5,773,292 A | * | 6/1998 | Bander ....................... 435/332 |
| 5,885,808 A | * | 3/1999 | Spoomer et al. ......... 435/172.3 |

FOREIGN PATENT DOCUMENTS

| | | | |
|---|---|---|---|
| WO | | 93/17715 | * 9/1993 |

OTHER PUBLICATIONS

Ghose et al (1983) Meth. Enzymol 93:280–333.*

Pai & Pastan (1993) JAMA 269:78–81.*

Williams et al (1990) Inst. J. Rad. Oncol. Biol. Phys. 19:633–642.*

Perälä–Heape et al. (1991) Anticancer Res. 11:1327–32.*

Webster's Seventh New Collegiate Dictionary, G & C Merriam Co., Springfield, Mass, p. 970, 1969.*

Kimmel et al, J. Neurosurg. 66:161–171, 1987.*

Osband et al, Immunol. Today, 11:193–195, 1990.*

Hird et al, "Genes and Cnacer" Carney et al., Ed, John Wiley and Sonds LTS, 83–89, 1990.*

Harlow and Lane, Antibodies, A Laboratory Manual, Cold Spring Harbor Laboratory, Cold Spring Harbor, p. 111–142, 1988.*

* cited by examiner

*Primary Examiner*—Susan Ungar
(74) *Attorney, Agent, or Firm*—Merchant & Gould P.C.

(57) ABSTRACT

Bioactive materials, e.g. therapeutic agents for treating a condition that afflicts a patient, are delivered to the afflicted organ in a site-specific manner by coupling the bioactive agent to an antibody or fragment or derivative thereof that recognizes a substance unique to that organ. For example, therapeutic agents for treating conditions of the prostate gland such as adenocarcinoma of the prostate, benign prostatic hypertrophy and prostatitis can be delivered to the prostate by coupling the thereapeutic agent to an antibody against a substance secreted by the prostate, e.g. prostatic specific antigen or prostatic acid phosphatase.

6 Claims, 9 Drawing Sheets

(8 of 9 Drawing Sheet(s) Filed in Color)

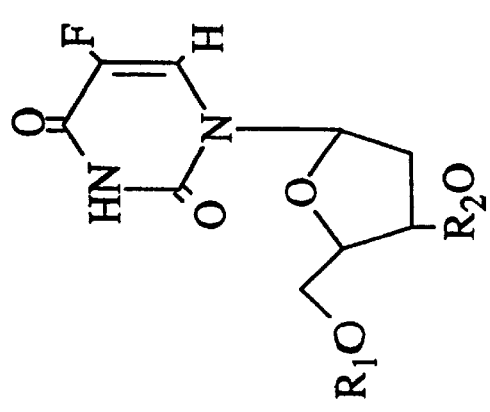

1. $R_1$=H  $R_2$=H
2. $R_1$=HPO$_4$  $R_2$=H
3. $R_1$=HPO$_4$-biotin  $R_2$=antibody IgG
4. $R_1$=HPO$_4$  $R_2$=fluorescein
5. $R_1$=POOHOC$_6$H$_4$NH$_2$  $R_2$=H
6. $R_1$=POOHOC$_6$H$_4$NH-fluorescein  $R_2$=H
7. $R_1$=POOHOC$_6$H$_4$NH-fluorescein  $R_2$=antibody IgG-rhodamine 1. 5'-fluoro-2'-deoxyuridine
2. 5'-fluoro-2'-deoxyuridine 5'monophosphate
3. Rabbit anti-PSA IgG-5'-fluoro-2'-deoxyuridine-biotin
4. 5'-fluoro-2'-deoxyuridine 5'monophosphate-fluorescein
5. 5'-fluoro-2'-deoxyuridine 5' (p-aminophenyl) monophosphate
6. 5'-fluoro-2'-deoxyuridine 5' (p-aminophenyl) monophosphate-fluorescein
7. Rabbit anti-PSA IgG-rhodamine-5'-fluoro-2'-deoxyuridine-5' (p-aminophenyl) monophosphate-fluorescein

FIG. 1

TARGETING OF ORGANS BY IMMUNOCONJUGATES

This application claims benefit to provision application No. 60/001,982, filed Aug. 3, 1995, now abandoned.

GOVERNMENT SUPPORT

The present invention was made with support from the Department of Veteran Affairs. The U.S. government may have certain rights in the invention.

BACKGROUND OF THE INVENTION

Cancer, the second highest cause of death in the U.S.A., is one of the most dreaded diseases. Unfortunately, the incidence of many types of cancer (such as prostate, breast, ovary, colon, pancreas, lung) has been increasing during the last 25 years. In addition, numerous infectious diseases, many of which are drug resistant, are becoming prevalent in the industrialized world or are moving into the industrialized world from the non-industrialized world. All solid organ tumors (some are identified above) possess many clones or subpopulations of cancer cells, which make them heterogeneous tumors that are very difficult to treat. A common problem in developing therapies for each of these categories of diseases is targeting the therapeutic molecule(s) to many clones of tumor cells that may be found in several loci in patients.

Among cancers, adenocarcinoma of the prostate (CAP) is the most prevalent neoplasm and is the leading cause of cancer death in males in the U.S.A. In nearly 50% of patients, neoplastic prostate cells have spread at the time of diagnosis. Benign prostatic hypertrophy (BPH) results in over 400,000 surgical procedures in the U.S.A., which usually are done to correct urinary obstruction. This makes benign prostatic hypertrophy the second most common reason for surgery in males in the U.S. Human prostate cancer, benign prostatic hypertrophy, and prostatitis require about 5 million physician visits, 900,000 hospitalizations with 40,000 deaths, and costs over $3 billion/year in the U.S.A. Similar estimates can be made for the industrialized countries of Europe. In addition, the World Health Organization has determined that BPH and prostatitis are worldwide health problems. Clearly, the current and potential need for a treatment for these conditions is very large.

The current chemotherapeutic and endocrine treatments for prostate cancer as well as benign prostatic hyperplasia suffer from at least two major limitations, lack of drug/treatment specificity and drug resistance. Lack of specificity has led to utilization of higher doses of chemotherapeutic and endocrine drugs, which adversely affect many organs without tumors and have numerous unpleasant side effects in patients. Furthermore, drug resistance (chemoresistance), usually due to development of multidrug resistance proteins (Mdr) such as P-glycoproteins (Pgp), often negates the treatment effects in a relatively short time. Drug resistance varies from tumor to tumor and in different types of tumors. Most patients who develop chemoresistant tumors usually do not respond to other chemotherapeutic drugs or their combinations. This results in treatment failure and death of the patient, usually within a year. Because of the potential for drug resistance, the specific drug must act on many clones (or subpopulations) of tumor cells directly and quickly to be effective, before they develop drug resistant proteins.

To overcome the limitations imposed by drug resistant proteins, the chemotherapeutic drugs must be highly specific to the target cells such as neoplastic cells of prostate, breast, ovary, colon, or other solid organ tumors. Furthermore, the drug should have minimum to no effects on the unrelated organs or tissues as well as minimal side effects in patients.

The existing treatments for prostate cancer include surgery, radiation, endocrine therapy, and chemotherapy. These often have limited value, especially in patients with metastatic disease because these treatments are unable to specifically target metastatic cancer cells. Therefore, new approaches are required to improve treatment effects on prostate cancer as well as other solid organ neoplasms, such as those in the breast, ovary, cervix, colon and lung. There is a need to target bioactive compounds in other diseases and disorders as well.

Therefore, there is a need for highly specific drugs that could overcome the above limitations and at the same time target many subpopulations of neoplastic cells or dysfunctional tissues or organs. For cancers, it is important to target the tumors before they develop drug resistance for improvements in the treatments of prostate and other cancers.

SUMMARY OF THE INVENTION

The concept of targeting a specific organ requires consideration of biological characteristics of the normal organ as well as its tumors and disease states. For example, in human prostate, prostatic specific antigen (PSA) and prostatic acid phosphatase (PACP) are organ-specific enzymes and are usually secreted by prostatic epithelial cells in sufficient amounts. Therefore, the biological properties of these enzymes can be used to develop highly specific drug conjugates that would then specifically target prostatic epithelial cells, but not other types of cells in other organs which usually do not secrete these enzymes.

The present invention provides compositions and methods for delivering bioactive compounds to target organ tissues. One embodiment Of the method includes an immunoconjugate that recognizes a substance in a solid tissue. The immunoconjugate includes a polyclonal or monoclonal antibody, preferably a polyclonal antibody, as a binding or recognition moiety and a bioactive agent. The solid tissue can be a normal or benign tissue, preferably a tumor. In a specific embodiment, the tumor is a prostate tumor.

A polyclonal antibody has greater potential of recognizing many more epitopes of the substance associated with the solid tissue, e.g. PSA or (PACP) in the case of the prostate, than a monoclonal antibody. Therefore, a polyclonal antibody would recognize more of the clones or tumor cells than a monoclonal antibody. Thus, an immunoconjugate prepared utilizing polyclonal antibody IgG or its fragments will bind to most of the target cells that are producing an organ-specific enzyme, moiety, or substance.

The binding moiety is a molecule that recognizes and can bind to a molecule, substance and the like which is unique to the solid tissue. The binding moiety can be a polyclonal antibody or derivative or fragment thereof. Preferably, the binding moiety is an IgG. A conjugate in which the binding moiety is an antibody or antibody fragment that is conjugated to a bioactive substance, e.g. chemotherapeutic, hormonal or cytotoxic drugs, produces an immunoconjugate.

The bioactive agent is a molecule that modifies a biological or biochemical response or action, that modifies the activity of a cell or biomolecule, or that affects an organism or part thereof. A preferred bioactive agent is a chemotherapeutic agent.

One embodiment of the invention is a method for delivering a bioactive substance to a target solid tissue in an animal which includes administering to the animal an immunoconjugate that includes a binding moiety and a bioactive agent. In the method, the amount of immunoconjugate administered is effective to result in delivery of sufficient bioactive substance to the solid tissue to have the desired effect. The method can be used in intact humans or animals, or in experimental systems such as organ culture.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 illustrates the structural formulae of some of the active agents useful in the present invention. The presentation of the figure is patterned after Goelach et al., Bioconjugate Chem., 2:96–101, 1991.

DETAILED DESCRIPTION OF THE PREFERRED EMBODIMENT

Figure 2:
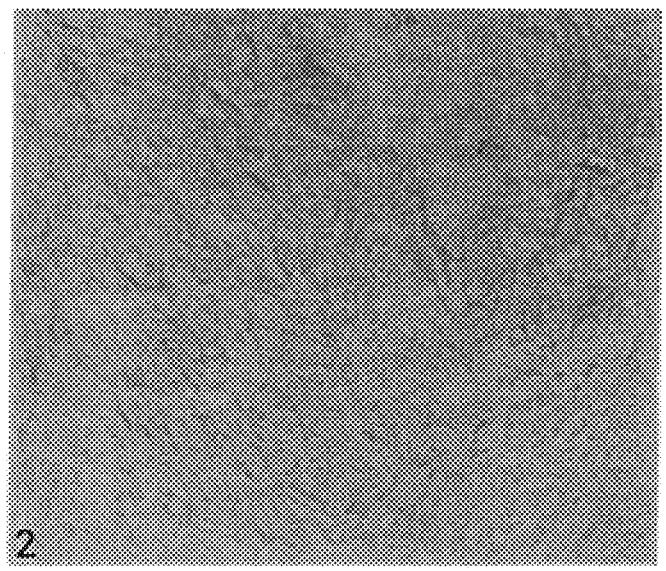
FIGS. 2–13 are micrographs resulting from in vitro experimental procedures discussed below.

Delivery of an active substance to the site of its action is necessary for the active substance to have its desired effect. One way to deliver a bioactive substance or agent to a site where it has activity is to form a conjugate in which the bioactive agent is linked to another molecule that has affinity for the organ to be treated. That is, a biologically active agent can be linked to a molecule that has specific affinity for the organ on which the bioactive substance is to exert its effect.

Such conjugates can take a variety of forms. A bioactive agent can be linked to a small molecule that enters a cell or organ. A conjugate can be formed between a bioactive agent and a protein or peptide hormone that is recognized by a particular type of cell. In addition, there are numerous other types of proteins or polypeptides that can serve to deliver a bioactive agent to the desired organ, tissue, or cell. A preferred protein is an antibody that recognizes a molecule, a substance, or an epitope which is unique to a particular organ. The antibody is preferably polyclonal, but monoclonal antibodies could be used as well. The antibody can be an active portion of an antibody such as FAB or FC fragments. Conjugates between a bioactive agent and an antibody are called immunoconjugates.

The immunoconjugates of the present invention target a desired organ using antibodies with affinity for a substance on the cell, tissue, or organ to carry bioactive substances to the cell. Antibodies can be produced against substances found in human solid tissues and tumors of tissues such as prostate, breast, ovary, colon, pancreas and lung, and conjugated with bioactive agents to produce specific immunoconjugates. The conjugates which include the bioactive agent can concentrate the bioactive agent at the desired organ site and diminish unwanted side effects associated with non-specific drugs or bioactive agents. Furthermore, the binding of bioactive agents to antibody molecules can protect the bioactive agent from enzymatic degradation and prevent its rapid excretion. Selective delivery of the immunoconjugates to the target sites can also lead to the use of smaller doses of bioactive agents while maintaining effective treatment.

Immunoconjugates can be cytotoxic or can have other bioactivity. Typically, immunoconjugates have their effect inside the target cell and/or plasma membranes and specific receptors on cell surfaces. The immunoconjugate can enter the cell by several mechanisms, such as endocytosis by the target cells, by diffusion, by facilitated diffusion, or by active carrier-mediated transport. Some conjugates enter the target cells by endocytosis and release their bioactive substance at the lysosomal membrane. Some immunoconjugates are not degraded at the surface and enter the cells by endocytosis. The success of immunoconjugates at delivery of a bioactive substance can depend upon transport related factors such as the ability of the conjugate to localize and persist at the cell or tissue and its intracellular or intratissue penetration and metabolism.

The immunoconjugate can exert its effect without entering the cell as well. Internalization of the immunoconjugate may not be necessary since the conjugate may exert its bioactivity by, for example, action within the cell membrane. The immunoconjugate may bind to specific receptors on the cell surface and elicit an inhibitory response in the target cells, but not in non-target tissues. It may also be internalized by endocytosis, diffusion, or active transport mechanism.

Another mechanism involves inhibition of DNA synthesis in the target cells because the immunoconjugate will reach the target cells via antibody IgG. For example, a chemotherapeutic drug such as 5-fluorouracil or its derivatives inhibit thymidine synthetase (thymidine synthase) and thus, DNA synthesis is inhibited in target cells. Without DNA synthesis, a neoplastic or any type of cell can not divide or proliferate, and cell death will follow. In treating conditions of the prostate, for example, with the specificity of PSA-IgG-drug conjugate, the immunoconjugate would bind to prostatic tumor cells and would inhibit DNA synthesis in the cell type of choice. Thus, the growth of the tumor is greatly decreased, and cell death will be greatly enhanced. This mechanism will function in prostate cancer and benign prostatic hyperplasia, including some breast and ovarian tumors producing PSA.

Immunoconjugates can show activity in a variety of metabolic disorders, disease states, and physiological conditions. For example, conjugates can inhibit the growth of tumors of androgen-sensitive organs such as testis, ventral prostate, and seminal vesicle, all of which have androgen-sensitivity. Immunoconjugates may also be useful to target bioactive molecules to the locus of disease in conditions such as infectious diseases including those caused by viruses or parasites, and metabolic and inflammatory disorders of the organs, and the like. Immunoconjugates show activity against human disorders, such as prostate cancers or breast cancers, and in animal diseases and animal models of human diseases. The present immunoconjugates are particularly desirable for targeting solid organ cancers.

As one example, antibody IgGs to PSA or PACP proteins, when conjugated to 5-Fluoro-2'deoxyuridine (5-FU-2'd) or other chemotherapeutic agents, can form immunoconjugates that bind specifically to PSA or PACP antigens present in prostate (neoplastic and non-neoplastic) cells in the prostate gland. Since the immunoconjugate binds preferentially to PSA or PACP antigens in the prostatic cells, the specific immunoconjugate would readily reach the target cells and inhibit DNA synthesis and elicit cell death and/or reduce, or even abolish, cell proliferation much before the prostatic cells are able to develop multidrug resistant proteins. Non-tumor conditions such as prostatitis also can be treated in this manner.

Some breast and ovarian tumors have been shown to produce prostatic specific antigen, but not prostatic acid phosphatase. Therefore, in PSA-producing tumors, PSA-IgG-drug conjugate could be used to target neoplastic cells in the organs, much like prostatic tumors. In these tumors, the immunoconjugate would also inhibit thymidine synthase and thus, DNA synthesis. With the inhibited DNA synthesis, the tumor will cease to grow or proliferate, and cell death would occur.

Antibodies can be raised to a variety of substances, haptens, proteins, or antigens. As used herein, antigen refers to a substance or molecule recognized or bound by an antibody. The distribution of the antigen through the organism or cell determines where in the organism the antibody will bind and be localized or delivered. An antigen that is distributed throughout an organism or body would localize the antibody or immunoconjugate throughout that organism or body. Conversely, an antigen that is found only on a particular cell type in a particular organ would localize the antibody or immunoconjugate to that specific cell population in that specific organ, Furthermore, some antigens are expressed only in dysfunctional or infected cells or organs, which allows them to be used to target antibodies or immunoconjugates to that particular cell type or organ.

For example, as noted above, PSA and PACP are antigens which are uniquely produced by the prostate gland in humans. As a further example, in mammals the mammary gland uniquely amongst all organs produces casein. Casein would therefore be a suitable molecule or substance to use to localize an immunoconjugate to the mammary gland. Furthermore, casein is readily available as a reagent to use to raise antibodies from numerous sources. Polyclonal (or monoclonal) antibodies raised against casein can then be used to form immunoconjugates.

In addition, the human mammary gland secretes caseins (alpha, 27,300 daltons and beta, 24,000 daltons) during lactation, but small amounts are also elaborated in differentiated mammary glands of non-pregnant, adult women during the reproductive cycle. Caseins are usually part of mucins that are sometimes called milk mucins. There are at least 5 types of mucins, of which MUC 1 is well characterized, MUC 2 to 5 less so (Sandra et al., In: Breast Epithelial Antigens, R. L. Ceriani, editor, Plenum, N.Y., 1991). MUC 1 is the only human mucin for which a full length cDNA has been described. Many different types of antibodies against mucins have been produced around the world, and it appears that for breast cancer, more than 90% of them react with mammary mucins (Xing and McKenzie In: Breast Epithelial Antigens, R. L. Ceriani, editor, Plenum, N.Y., 1991; Cancer Cells, 2:75–78, 1990). Mucins are transmembrane molecules and can be demonstrated by polyclonal antiserum (CT-1). The antiserum reacts with MUC 1 and is available from commercial sources. Antibodies against caseins or mucins could also be produced in many research laboratories using the methods described below.

The human gastric epithelium and its neoplasms also produce mucins (Ho et al., Cancer Res., 55:2681–2690, 1995; Ho and Kim, Cancer Biol., 2:389–400, 1991; Ho et al., Cancer Res., 53:641–651, 1993) and thus this is another example of a tissue that can be treated with the present invention. For example, rabbit anti-MUC 1 antibody IgG (i.e., against MUC 1 mucin found in breast and colon tissues) can be conjugated to 5-Fu and its derivatives. The anti-MUC 1 IgG-drug-immunoconjugates can be tested in in vitro and in vivo conditions much as PSA-IgG-drug immunoconjugates. Thus, the principle applied for the PSA-IgG-drug-immunoconjugate is applicable for delivery by anti-MUC 1 (also antibodies against other Mucs) to breast and colon cancers.

Recently, Sinha et al. (Anat. Rec., 241:3531–362, 1995) and others (Folkman and Shing, J. Biol. Chem., 267:10931–10934, 1992; Bigler et al., Human Pathol., 24:220–26, 1993; Weidner et al., Am. J. Pathol., 143:401–409, 1993; Klagsburn and D'Amore, Ann. Rev. Physiol., 53:217–239, 1991) have shown that formation of new blood vessels (i.e., angiogenesis or neovascularization) is required for the growth of solid organ tumors (such as prostate, breast, colon, lung, ovary). Angiogenesis usually precedes growth of tumor and invasion of neoplastic cells in the adjacent stroma. This often leads to invasion of the blood vessels or lymphatics by neoplastic cells and the formation of metastatic tumors elsewhere in the body. Sinha et al. (see above) showed that cathepsin B, a cysteine protease, is involved in the breakdown of basement membranes in the angiogenic blood vessels of human prostate cancer. Therefore, endogenous inhibitors (such as cystatin A, B, and/or C) of cathepsin B could be used to inhibit degradative roles of cathepsin B at the sites of angiogenesis or tumor invasion. For example, cystatin A could be conjugated to PSA-antibody IgG using the earlier described methods and then the PSA-IgG-cystatin A immunoconjugate could be used to inhibit formation of new blood vessels at the tumor sites. Since cathepsin B is also involved in tumor invasion, PSA-IgG-cystatin A or B would also inhibit tumor cell invasion of the stroma. Without angiogenesis, growth of prostate tumor would not occur. Likewise, PACP-IgG could be used for conjugating cystatin A, B or C.

Angiogenesis is essential for tumor growth (Sinha et al., cited above) as well as the growth of normal tissues during wound healing and other repairs. A variety of chemicals, agents, and/or inhibitors (such as Thrombospondin: Koch et al., Pathobiol., 61:1–6, 1993; Heparin: Norby, Haemostasis 23 (Suppl 1):141–149, 1993; Heparin adipic hydrazide with/without cortisol: Thorpe et al, Cancer Res., 53:3000–3007, 1993; medoxyprogesterone: Folkman, Adv. Cancer Res., 43:175–202, 1985; Klagsburn and D'Amore, Ann. Rev. Physiol., 53:217–239, 1991) have been proposed to inhibit angiogenesis. Most of these agents have not been successful because they could not be delivered to the specific sites of new blood vessel formation near the tumors. It is obvious that inhibition of blood vessel formation throughout the human body will have numerous detrimental effects. Using the present immunoconjugation methods, the above inhibitors/molecules could be conjugated and thus, the newly formed immunoconjugate will be delivered to the target sites to inhibit formation of new blood vessels which are often very closely associated with the prostatic glandular epithelium. In other words, a variety of angiogenic inhibitors can be conjugated with PSA and/or PACP-IgGs and delivered to the angiogenic sites where they would induce inhibition of angiogenesis. Delivery of angiogenic inhibitors via PSA-IgG should inhibit tumor growth at the early stages as well as tumor growth and tumor cell invasion in the stroma.

The roles of receptors (such as androgen, estrogen, or progesterone) in protein synthesis have been defined for human and animal organs (Luke and Coffey, J. Androl., 15:41–51, 1994; DeWinter et al., Am. J. Pathol., 144:735–746,1994; Srinivasan et al., Micros. Res. & Techniques, 30:393–304, 1995; Khan et al., Cancer Res., 54:993–997, 1994; O'Malley and Tsai, Biol. Reprod., 46:163–167, 1992). The target organ cells will not proliferate in the absence of protein synthesis. For example, androgen receptors are found in a variety of organs and tissues (such as prostate, genital skin, testis). Any immunoconjugate should not target normal organs. In contrast, PSA occurs predominantly in the prostate gland. This situation can be remedied by using PSA-IgG (or PACP-IgG), which are organ-specific markers. Using PSA/PACP-IgG, as a carrier protein, much as it has been used for 5-Fu and its derivatives, the anti-receptor antibody IgGs can be delivered to the target organ tumors. In other words, PSA-IgG will function as a carrier molecule for anti-androgen receptor IgG to the target prostate epithelial cells and their tumors. The PSA-IgG-anti-androgen receptor IgG will then inhibit protein synthesis in prostatic cells. Therefore, when PSA-IgG is conjugated to anti-androgen receptors, PSA-IgG will deliver anti-androgen receptor antibody IgG only to prostate cells, both epithelial and stromal, and not to testis or genital skin which do not possess prostatic specific antigen. This property makes this double immunoconjugate very specific for inhibiting protein synthesis in prostatic tumors. Likewise, when PSA-IgG is conjugated to anti-estrogen and/or progesterone receptors, these receptors will be carried to a specific organ (some breast and ovarian tumors produce PSA) via PSA-IgG. In turn, this will inhibit protein synthesis in breast-ovarian tissues and tumor growth will be inhibited.

In summary, with respect to prostate treatment in accordance with the present invention, PSA-IgG (or PACP-IgG) functions as a carrier molecule to which a variety of molecules such as chemotherapeutic drugs/toxins, inhibitors to angiogenesis, enzymes, and even antibody against steroid receptors can be conjugated and delivered in a specific manner to the target tissues. Multiply-coupled agents also are possible. For example, a PSA-IgG-anti-androgen receptor-IgG-drug combination might be used. The present invention can be applied to other organs using antibodies to substances found in those organs.

Production of monoclonal and polyclonal antibodies against a variety of antigens, peptide and other agents/molecules has become established in research and commercial laboratories (Immunochemical Methods by R. J. Mayers and J. H. Walker, editors, Academic Press, 1987; Practical Immunology, L. Hudson and F. C. Hay, editors, Blackwell Sci. Publ., 3rd edition, 1999; Antibody Techniques by V. S. Malik and E. P. Lillehoj, editors, Acad. Press, 1994; Monoclonal Antibodies: Principles and applications, J. R. Birch and E. S. Lennox, editors, Wiley-Liss, 1995). The following protocol can be used to produce polyclonal antibody against PSA as well as PACP. Prostatic specific antigen or prostatic acid phosphatase molecules will be isolated from semen of normal healthy males and purified of contaminating enzymes, proteins, and other substances (see for details, Practical Immunology, L. Hudson and F. C. Hay, editors, Blackwell Sci. Publ., 3rd edition, 1989; Antibody Techniques by V. S. Malik and E. P. Lillehoj, editors, Acad. Press, 1994). The affinity purified enzymes/antigens will be suspended in phosphate buffer saline NaCl (0.5 ml) complete with Freund's adjuvant (0.5 ml). The suspension is then injected intramuscularly at multiple sites in male New Zealand rabbits. Two weeks after the initial does, a booster injection is given intramuscularly. Booster injections are repeated up to four times at biweekly intervals. Pre-immune serum is collected before injecting the antigen/enzymes. After immunizations, serum is collected again and purified for the immunoglobulin G (IgG) fraction, i.e., traces of contaminating antibodies and other immunoglobulins will be removed by solid-phase absorption techniques. The antibody will also be purified against PSA/PACP affinity columns. The specificity and purity of PSA-IgG can be established by radioimmunoassay and chemiluminescence immunoassay techniques (see Practical Immunology, L. Hudson and F. C. Hay, editors, Blackwell Sci. Publ., 3rd edition, 1989; Antibody Techniques by V. S. Malik and E. P. Lillehoj, editors, Acad. Press, 1994). Polyclonal antibodies against PACP and mucins (including casein alpha or beta) could also be prepared using the above cited literature. In fact, most of these antibodies are readily available from commercial sources and their production could be customized for specific needs at a very reasonable cost. In summary, production of both monoclonal and polyclonal antibodies against selected molecules identified in this application is not a limitation for preparing immunoconjugates.

Polyclonal antibody against PSA is most suitable because it recognizes nearly all epitopes of prostatic specific antigen in human prostate whereas monoclonal antibody will recognize a single and similar epitopes of PSA. For some prostate cancer cases, a cocktail of monoclonal antibody IgGs could be made and then the IgGs would be conjugated to chemotherapeutic drugs or toxins. In well-differentiated tumors, especially when prepared for a specific patient, whether monospecific polyclonal or monoclonal antibody against PSA, the latter IgGs would be conjugated. Much as the polyclonal IgG-drug-immunoconjugates, monospecific or monoclonal antibody IgGs would be conjugated and the later immunoconjugates could prove to be effective. Likewise, monospecific/monoclonal PACP antibody IgGs will be conjugated with chemotherapeutic drugs and toxins/inhibitors.

Monoclonal or polyclonal antibodies against PSA and PACP can be produced using a variety of techniques (see Practical Immunology, L. Hudson and F. C. Hay, editors, Blackwell Sci. Publ., 3rd edition, 1989; Antibody Techniques by V. S. Malik and E. P. Lillehoj, editors, Acad. Press, 1994). Polyclonal antibody could be produced in rabbit using monospecific PSA antigen, much as it was done for cathepsin B (Sinha et al., Prostate, 26: 171–178, 1995). Alternatively, a cocktail of monoclonal PSA antibody will be produced using mice, rat, or hybridoma technology (Antibody Techniques by V. S. Malik and E. P. Lillehoj, editors, Acad. Press, 1994) or two or more monoclonal antibodies will be mixed together to get a cocktail of antibody IgGs. Regardless, the IgG molecules, whether derived from polyclonal and monospecific or monoclonal antibody methods of preparation, would function as carrier proteins for conjugating a variety of agents/drugs. PSA-IgG molecule would deliver the conjugated drug/toxins/other agents to human prostatic tumors. In the event there is immunologic reaction against a given immunoconjugate, immunosuppressive drugs could be used. However, there should not be any immunologic reactions before 14 to 18 days after the initiation of treatment with an immunoconjugate and this ought to be established for a given immunoconjugate.

The present immunoconjugates can include a variety of bioactive agents that exert a variety of effects. Some bioactive agents are so potent that exposure of the cell to a single molecule of the bioactive agent is sufficient to have the desired biological effect, such as killing the cell. But bioactive agents can have varying degrees of potency and can work by many mechanisms. Mechanisms for bioactive agents or toxins include inactivating DNA and protein synthesis or recognizing specific proteins or protein complexes in the cell and interfering with their action. Bioactive agents can be enzyme inhibitors, receptor antagonists, molecules that interfere with macromolecular interactions, antimetabolites, and the like.

The bioactive agent can be a chemotherapeutic agent such as methotrexate, doxorubicin, adriamycin, cis-platinum, tamoxifen, estrogen, progesterone, mitomycin C, 5-fluorouracil, or 5-fluoro-2'-dioxyuridine, vinblastin, doxorubicin and the like. Bioactive agents such as chemotherapeutic agents or anti-metabolites can exert bioactivities such as inhibiting DNA synthesis, either directly or indirectly, in tumors and cancers such as those of the breast, colon, and ovary. The bioactive agent can be a drug such as daunomycin or ouabain. The bioactive agent can be a radio-labeled compound or a radionuclide such as $I^{125}$ or $I^{131}$ and the like. The bioactive agent can be a plant toxin or a bacterial toxin such as ricin, abrin, diphtheria toxin, or cholera toxin.

Patient treatment using the method of the present invention involves administering therapeutic amounts of the immunoconjugate composition. In the context of the present invention, the terms "treat" and "therapy" and the like refer to alleviate, slow the progression, prophylaxis, attenuation or cure of existing disease. An immunoconjugate composition may be formulated with conventional pharmaceutically acceptable vehicles for administration by injection. These vehicles comprise substances which are essentially non-toxic and non-therapeutic such as water, saline, Ringer's solution, dextrose solution, Hank's solution, or the like. It is to be understood that immunoconjugate formulations may also include small amounts of adjuvants such as buffers and preservatives to maintain isotonicity, physiological and pH stability. Preferably, the immunoconjugate is formulated in purified form substantially free of aggregates and other protein 0.001 to about 10 mg/ml and preferably from about 0.01 to about 1.0 mg/ml. The concentration may vary depending upon conjugate and concentration of IgG and drug molecules.

The dose of the immunoconjugate formulation to be administered will depend upon the patient and the patient's medical history, and the severity of the disease process. However, the dose should be sufficient to suppress the disease state, for example to slow or stop the progression of prostate cancer. Dosages for adult humans envisioned by the present invention and considered to be therapeutically effective will range from about 0.001 to about 10 mg/subject/day and preferably from about 0.01 to about 2.0 mg/subject/day; however, lower and higher amounts may be more appropriate. In addition, to the extent that the present immunoconjugate includes a bioactive agent that is currently used for treating the condition in question, current dosage regimens can be taken into consideration, it being noted that the administration of the bioactive agent in the form of the immunoconjugate in the present invention should allow the administration of lower levels of the bioactive agent to achieve the desired beneficial effect.

The immunoconjugates can be delivered directly to the organ to be treated. They also can be administered directly to the blood stream, e.g. by intravenous injection or intramuscular administration. Oral administration may be possible in some cases. The immunoconjugates should be formulated with appropriate carriers depending upon the intended mode of administration.

The invention will be further described by reference to the following examples, which should be considered to be non-limiting.

Methods for Producing Antibodies to Substances in Solid Tissues

Production of monoclonal and polyclonal antibodies against a variety of antigens, peptide, and other agents/ molecules has become established in research and commercial laboratories and has been extensively reported in the literature (Immunochemical Methods by R. J. Mayers and J. H. Walker, editors, Academic Press, 1987; Practical Immunology, L. Hudson and F. C. Hay, editors, Blackwell Sci. Publ., 3rd edition, 1989; Antibody Techniques by V. S. Malik and E. P. Lillehoj, editors, Acad. Press, 1994; Monoclonal Antibodies: Principles and applications, J. R. Birch and E. S. Lennox, editors, Wiley-Liss, 1995). The following protocol can be used to produce polyclonal antibody against PSA as well as PACP. Prostatic specific antigen or prostatic acid phosphatase molecules will be isolated from semen of normal healthy males and purified of contaminating enzymes, proteins and other substances (see for details, Practical Immunology, L. Hudson and F. C. Hay, editors, Blackwell Sci. Publ., 3rd edition, 9189; Antibody Techniques by V. S. Malik and E. P. Lillehoj, editors, Acad. Press, 1994). The affinity purified enzymes/antigens will be suspended in phosphate saline NaCl (0.5 ml) complete with Freund's adjuvant (0.5 ml). The suspension is then injected intramuscularly at multiple sites in male New Zealand rabbits. Two weeks after the initial dose, a booster injection is given intramuscularly. Booster injections are repeated up to four times at biweekly intervals. Pre-immune serum is collected before injecting antigen/enzyme. After immunizations, serum is collected again and purified for the immunoglobulin G (IgG) fraction, i.e., traces of contaminating antibodies and other immunoglobulins are removed by solid-phase absorption techniques. The antibody is then purified against PSA/PACP affinity columns. The specificity and purity of PSA-IgG should be established by radioimmunoassay and chemiluminescence immunoassay techniques (see Practical Immunology, L. Hudson and F. C. Hay, editors, Blackwell Sci. Publ., 3rd edition, 1989; Antibody Techniques by V. S. Malik and E. P. Lillehoj, editors, Acad. Press, 1994). Polyclonal antibodies against PACP and mucins (including casein alpha or beta) could be prepared in a similar manner. In fact, most of these antibodies are readily available from commercial sources and their production could be customized to specific needs at a very reasonable cost. In addition, there are companies (such as American Biogenetic Sciences, Inc. New York, N.Y.) who market humanized antibodies for injections and treatment in patients. The humanized PSA and PAcP antibodies then would be conjugated with the selected drugs, toxins or other bioactive agent. Humanization of the antibody will greatly reduce or abolish adverse effects of foreign proteins in patients. Immunoconjugates to be tested in humans or animals should be made with sterile, pyrogen-free solution, and prepared in pharmaceutically acceptable, buffered, isotonic aqueous solution. Exotoxins and endotoxins should be removed before injections in humans and animals. All of these techniques are familiar to those skilled in this art and thus are not discussed in detail.

Methods for the Conjuration of an Antibody to a Bioactive Substance

There are a variety of methods to conjugate bioactive substances to antibodies, or other targeting proteins, to form immunoconjugates. The bioactive substance can first be conjugated to a carrier protein, such as human serum albumin, and this complex is then chemically linked to an antibody. Alternatively, the bioactive substance can be linked to the antibody, or other targeting protein, either directly or through a small organic or inorganic linker. Examples of such linkers include cis-aconitase and other linkers known in the art.

Another linker is Sulpho-SMPB Succinimidyl-4-(p-maleimidophenyl) butyrate (Pierce Chem. Co., Rockford, Ill.). SMPB aromatic crosslinkers have been shown to improve the yield of immunotoxin conjugates (Myers et al., J. Immuno. Methods 121, 129–142, 1989; Pietersz, G. A. Bioconjugate Chem. 1, 89–95, 1990; Cumber et al., Methods Enzymol. 112, 207–225, 1985; Akerblom et al., Bioconjugate Chem. 4, 455–466, 1993).

Several methods have been used to conjugate PSA-IgG with 5-FU-2'd. For example, rabbit anti-human PSA antigen (Dako) was conjugated with 5-fluoro-2'-deoxyuridine 5'-p-aminophenylphosphate (Sigma, St. Louis, Mo.).

Conjugation of 5-Fu-2'-d or 5-FU-2'-d-5'-mp with PSA-IgG was accomplished using known conjugation and purification techniques (Myers et al., J. Immuno. Methods 121, 129–142, 1989; Pietersz, G. A. Bioconjugate Chem. 1, 89–95, 1990; Cumber et al., Methods Enzymol. 112, 207–225, 1985; Akerblom et al., Bioconjugate Chem. 4, 455–466, 1993; Whiteley et al., Biochem. 13, 2044–2050, 1974). Briefly, 5-Fu-2'-d-5'-mp was dissolved in 20 $\mu$l dimethylformamide (Myers et al., J. Immuno. Methods 121, 129–142, 1989) and 200 $\mu$l 100 mM PBS (pH 7.8) was added. A 5 mole excess of Sulpho-SMPB Succinimidyl-4-(p-maleimidophenyl) butyrate was dissolved in 100 MM phosphate buffer saline (PBS, pH 7.8) and then added to the above mixture. The later mixture was incubated at 25° C. for 30 minutes, after which the reaction was quenched with 2 mg bovine serum albumin (BSA) (10 mg/ml) in 100 mM PBS (pH 7.8) for 30 minutes at 25° C. The mixture was placed over a Pharmacia PD-10 column equilibrated with 100 mM PBS (pH 7.8). Column fractions were analyzed at 260 and 280 nm. The extent of conjugation was determined using UV Spectrophometer. The unconjugated rhodamine and fluorescein were removed by gel column chromatography (Whiteley et al., Biochem. 13, 2044–2050, 1974). Using methods of Whiteley et al. (Biochem. 13, 2044–2050, 1974), the purity of the PSA-IgG-drug was established. The Drug-Immunoconjugate was reactive to PSA by indirect immunoassay (Albrecht et al., Clin. Chem. 40, 1970–1971, 1994). Conjugation was also determined using UV spectrophotometry and immunoreactivity of PSA by chemiluminescence assay.

Similar methods have been used to conjugate PACP-IgG with 5-fluoro-2'-deoxyuridine. In this specific conjugate, approximately 67 molecules of 5-Fu-2'-d-5'-mp were conjugated/molecule of IgG. Chemotherapeutic drugs, rhodamine, and FITC were obtained from Sigma Chem. Co. (St. Louis, Mo.). Likewise, 5-fluoro-2'-deoxyuridine and 5-Fu-2'-d-5'-mp were conjugated with or without rhodamine or fluorescein. Drugs also were conjugated with FITC alone for control test purposes using similar procedures.

Human Prostate Tissue Collection

Human prostate tissue can be obtained from patients who undergo prostatectomy, cystoprostatectomy, or transurethral resection of the prostate (TURP). Prostatectomy samples are preferably collected from patients who have not been treated with cytotoxic or endocrine therapy before surgery. Data about the patients including age, grade and stage of the disease, and serum PSA values can be obtained and correlated before and after immunoconjugate treatment.

Samples can be dissected immediately after surgery for study. All prostate specimens should be collected aseptically and will include specimens representing tumors with a Gleason histologic scores of 2 to 10 (Human Pathol. 23:273–279, 1992). Benign prostatic hypertrophy samples can be obtained from patients undergoing prostatectomy or TURP for benign prostatic hypertrophy as established by histology. 'Normal' prostate samples can be collected from cystatectomy patients and can be used as control tissues.

Portions of prostate samples are then evaluated by histology to establish definitive diagnosis of either benign prostatic hypertrophy or cancer including the grades or histologic scores or both. Portions of colon, kidney, bladder and lung tissues will be collected to establish the specificity of immunoconjugates along with the negative and positive controls.

Preparation of Tissue or Organ Specimens

Prostate tumor and control prostate samples are dissected and processed according to protocols known in the art, then frozen in liquid nitrogen, or fixed in 10% buffered formalin and/or 3 to 4% buffered paraformaldehyde. In general, samples range from about 200 mg to 2 g. Excess tissue frozen in liquid nitrogen can be stored at –70° C. for future biochemical studies or fixed in formalin as needed. Randomly selected pieces can be used in organ culture and immunoconjugate treatments. Prostate and control tissues can be evaluated before and after organ culture and before and after drug treatments.

The procedures for sample preparation, fixation, embedding, sectioning, immunocytochemistry, in situ hybridization, and immunoelectron microscopy techniques are known in the art and will not be described in detail. Briefly, fixed and unfixed specimens can be embedded in OCT (Lab Tek Products, Naperville, Ill.), sectioned at 4 to 6 $\mu$m with a cytostat at –20° C., placed on specially cleaned poly-L-lysine coated slides and air dried in cold air. The remaining fixed specimens can be washed in 0.5 M NaCl for 10 minutes and processed for paraffin embedding. In general, pathological diagnosis is determined from cryostat or paraffin sections. Each specimen can be graded according to the Gleason grading system. (Human Pathol. 23: 273–279, 1992).

Prostate, colon, kidney, and lung samples can be evaluated histologically before and after short-term organ culture. Samples can be treated with PSA and PACP-IgG-immunoconjugates to establish optimum time and dilutions. PACP is an enzyme made predominantly by the prostate gland (Sakai et al., J. Urol. 149, 1020–1023, 1993; Sinha et al., Prostate 13, 1–15, 1988). A study was undertaken to demonstrate that human prostatic acid phosphatase (PACP) is also specific for prostatic epithelial glands and stromal tissues. Immunoconjugate effects can be evaluated in treated samples and compared with the untreated samples after localization of one or more markers. Markers include those for thymidine synthase, cell proliferation (PCNA), cell death (DNA fragments), and P-glycoprotein as well as unconjugated PSA and PACP antibodies. Negative controls can include normal rabbit serum. Such testing can establish immunoconjugate localization patterns and phenotypic characteristics of prostatic cells at light and electron microscopic levels.

Localization of Thymidine Synthase

Human prostate tissues collected and prepared as described above will be used to demonstrate localization pattern of thymidine synthase in immunoconjugate-treated and untreated samples. Since 5-Fu and its derivatives inhibit thymidine synthase, immunoconjugate-treated samples will show a markedly reduced thymidine synthase localization pattern in the affected cells than the untreated samples. Differential analysis will reveal the effects of immunoconjugate on the target cell DNA synthesis thereby decreased cell proliferation and increased cell death. Several studies have shown effects of 5-Fu and its derivatives on human tissues. (Goerlach et al, Bioconjugate Chem. 2, 96–101, 1991; Krauer et al., Cancer Res. 32, 132–137, 1992; Uchida et al., Anticancer Res. 10, 779–784, 1990; Johnson et al., Cancer Res. 55, 1407–1412, 1995; Liu & Santi; Biochim. Biophys. Acta 1209, 89–94, 1994). These drugs inhibit thymidylate synthetase in a variety of cell lines (Goerlach et al., Bioconjugate Chem. 2, 96–101, 1991; Krauer et al., Cancer Res. 32, 132–137, 1992; Uchida et al., Anticancer Res. 10, 779–784, 1990; Johnson et al., Cancer Res. 55, 1407–1412, 1995; Liu & Santi; Biochim. Biophys. Acta 1209, 89–94, 1994; Cobb, Cancer Immunol. Immunother., 28: 235–240, 1989).

Localization of Proliferation Cell Nuclear Antigen (PCNA)

Human prostate tissues were collected and prepared as described in Examples 2 and 3 above. These tissue specimens were exposed to antibodies that recognize PCNA and/or KI 67 both are used as markers of cell proliferation. Binding of these antibodies to the tissue was visualized by light microscopy. Results can be compared between conjugate-treated and untreated samples for drug induced inhibition of cell proliferation. Proliferating cells can be quantitated for objective analysis.

Localization of Fragmented DNA

The patterns of cell death, before and after immunoconjugate treatments of human prostate, can be established by localization of DNA fragments in apoptotic cells by the methods of Wijsman et al. (J. Histochem. Cytochlem. 41:7–12, 1993) and Landstrom et al. (Cancer Res., 54:4281–4284, 1994).

Briefly, prostate pieces treated with immunoconjugate and untreated piece can be fixed in 3 to 4% paraformaldehyde, embedded in paraffin or paraplast, sectioned at 4 to 6 $\mu$m, and mounted on poly-L-lysine coated slides. Sections will be deparaffinized, rehydrated, and digested with pepsin (0.5% pepsin) in HCl (pH 2) at 37° C. Digestion is stopped by washing in running water and then in buffer A (50 mM Tris-HCl, 5 mM $MgCl_2$, 10 mM B-mercaptoethanol, and 0.005% bovine serum albumin (Fraction V; Sigma Chemical Co., St. Louis, Mo.; pH 7.5) for 5 minutes. The tissue sample is then incubated at 15° C. with buffer A containing 0.01 mM dATP, dCTP, and dGTP (Boehringer-Mannheim, Indianapolis, Ind.) and 0.01 mM biotin-11-dUTP and 4 units/ml DNA polymerase 1 (Sigma). After blocking endogenous peroxidase in PBS containing 0.1% $H_2O_2$, sections are washed twice in PBS and incubated with horseradish peroxidase-conjugated avidin (Vector Labs., Burlingame, Calif.) diluted in 1:100 in PBS containing 1% BSA and 0.5% Tween 20 for 30 minutes at room temperature before developing with diaminobenzdine (Sigma). For negative controls, DNA polymerase is excluded in the nucleotide mixture.

Localization of P-glycoprotein

Analysis of immunohistochemical localization of monoclonal antibody C219 (Signet Lab., Dedham, Mass.) in prostate tissue samples allows estimation of the presence or absence of the drug resistant proteins (P-glycoprotein) in untreated and immunoconjugated-treated prostate cells. C219 recognizes an internal, highly conserved amino acid sequence found in both Mdr-1 and Mdr-3 isoforms of P-glycoproteins, which are found on a variety of tumors and cell lines. Localization techniques that determine the effect of dilution of the antibody in human prostate are known. For positive control, kidney tissues, drug sensitive SKOV3 cell line, and a variant of the cell line which is drug resistant can be used. The cells can be obtained from the American Type Culture Collection (Rockville, Md).

Techniques for Localization of Two or More Antigens

Some studies may require localization of two or more antigens or markers in the same sections. For example, the present methods can localize laminin by immunoperoxidase (IP) and cathepsin B by alkaline phosphatase (AP) in human prostate sections. The sequence of localization can be critical. For example, when laminin is localized by immunoperoxidase first and then cathepsin B by AP, suitable reaction products for both antigens are obtained. However, when the reverse order was employed, the alkaline phosphatase reaction products for cathepsin B were washed out.

Using these techniques, the distributions of immunoconjugate reaction products in relation to the localization of antibodies to thymidine synthase, PCNA, P-glycoprotein, DNA fragments, and other markers of a disease state or metabolic disorder can be defined.

Immunoconjugate Treatment of Prostate Cancer Tissues

Figure 3:
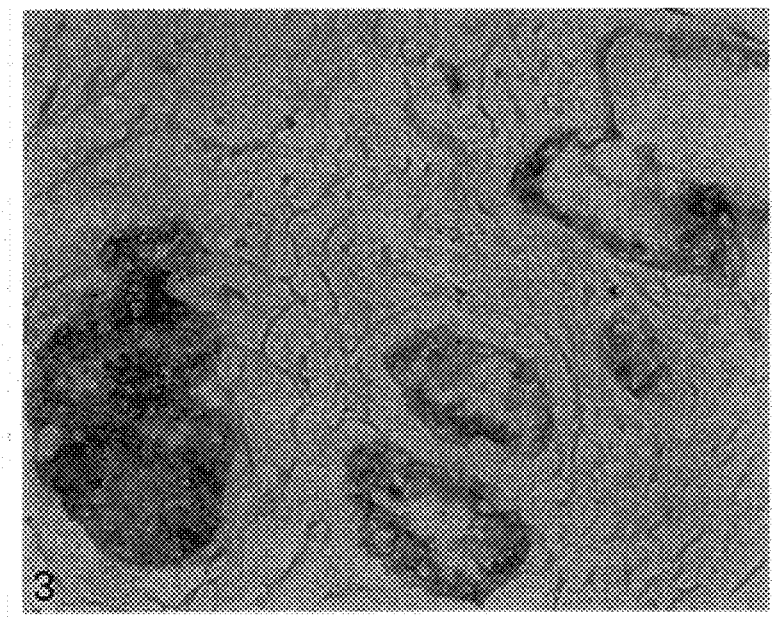

Antibody FOR IgG was conjugated with 5-FU-2'd or 5-FU-2'd-biotin. The PSA-immunoconjugate is suitable for studying human prostate cancer, benign prostatic hypertrophy, and prostate cell lines. The data shows that the immunoconjugate localized in glandular epithelia, but not in the stromal cells (FIGS. 2 and 3 discussed in detail below). Since PSA is secreted by epithelial cells, our study indicates that the PSA-immunoconjugate is specific to the prostate glands. This is notable because both benign prostatic hypertrophy and neoplastic tumors are of epithelial cell origin. These studies indicate that there should not be any problem in identifying the sites of immunoconjugate localization labeled with markers in untreated and treated human prostate and prostate cell lines.

Immunoconjugate Treatment of Prostate Cell Lines

The objective is to determine effects of PSA and PACP immunoconjugates (at 0, 1, 24, 48, 72 hours) on DU-145 and LN-CAP prostate cell lines and to establish patterns of thymidine synthase inhibition, reduced/decreased DNA synthesis, cell proliferation, cell death, and P-glycoprotein localizations. By comparing results between untreated and treated samples, one can establish the effects of immunoconjugates on these cell lines.

Conjugated drugs will reach the target sites because of the binding ability of the PSA-IgG antibody to PSA antigens which are usually found in prostatic epithelial cells. 5-Fu-2'-d or 5-FU-2'-d-5'-mp, when conjugated with PSA-IgG, could be localized in the same group of prostatic cells. Using conjugation and purification techniques (Whiteley et al., Biochem. 13:2044–2050, 1974), PSA-IgG was conjugated with rhodamine and 5-Fu-2'-d-5'-mp with fluorescein and then conjugated together. SMPB aromatic crosslinkers were used to improve the yield of immunotoxin conjugates. The extent of conjugation was determined by UV spectrophotometry. Immunoreactivity of the conjugate was established by chemiluminescence assay. Approximately, 81 molecules of 5-Fu-2'-d-5'-mp were conjugated/molecule of IgG. Rhodamine B isothiocyanate and Fluorescein isothiocyanate were purchased from Sigma.

Figure 9:
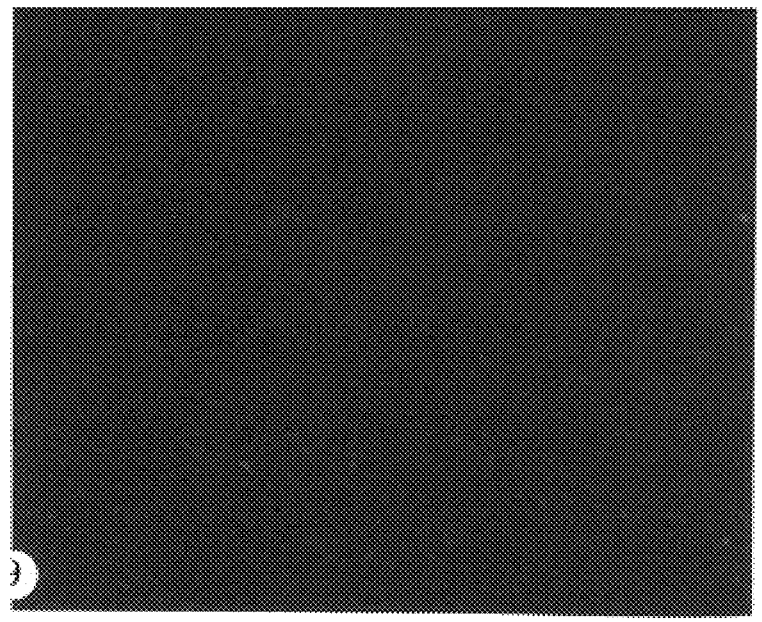

FIGS. 3, 4, 5, 6, 11 and 12 illustrate the localization of both PSA and 5-Fu-2'-d-5'-mp in the same group of cells. In contrast, the drug conjugated with fluorescein alone did not localize in epithelial cells (FIG. 9). These are discussed in more detail below.

Thymidylate synthase is the target enzyme for 5'-fluorouracil and its derivatives. The enzyme (EC 2.1.1.45) is involved in DNA synthesis. It is known that both 5-Fu-2'-d-5'-mp and 5-fluoro-2'-deoxycytidine-5'-monophosphate inhibit thymidylate synthase. Inhibition of DNA synthesis should result in decreased cell proliferation, increased cell death and increased synthesis of multidrug resistant proteins in prostate samples and prostate cell lines.

Animal Models of Human Prostate Cancer

Animal prostates do not express prostatic specific antigens or human prostatic acid phosphatase. However, human prostate pieces can grow when implanted in nude mice although they do not metastasize. The DU-145 human prostate cell line derived from a human prostate metastasized to brain does not metastasize in nude mice. The LN-CAP cell line can metastasize in adjacent tissues, if implanted with Matrigel in nude mice, but the pattern of metastasis is not similar to metastasis of human prostate cancer which metastasizes to bones, lymph nodes, brain, lungs and liver.

Human prostate cell lines PC-3, a derivative of the cell line 1-LN, and DU-145, can grow in nude mice. These cell lines do not express PSA antigens in cell culture or when grown in nude mice. The PSA-immunoconjugates did not recognize these cells lacking PSA antigens. This indicates that PSA-immunoconjugates are specific for cells containing PSA antigens and not for cells without the antigens.

Human prostate tumor pieces were transplanted into nude mice prostates. Human prostate tumor pieces were allowed to grow in nude mice for over a month and then the mice were sacrificed. Histological and PSA localization showed that human prostate tumor grew in a nude mouse prostate and the tumor cells localized PSA indicating that human tissue continues to express PSA in the animal model. This demonstrates that the PSA-immunoconjugate is specific for human prostate tumors with PSA antigens even after growing in nude mice. Human prostate pieces were implanted surgically under the ventral skin and inside the ventral prostate of nude mice. Mice were kept alive and at the end of the study they were sacrificed. Portions of tissues were collected and examined for human prostate pieces implanted earlier. PSA localization demonstrated presence of human prostate tissue. Thus, various parameters of drug effects can be readily established before undertaking in vivo treatment of prostatic tumors.

In vitro Studies

Since human prostatic specific antigen and human prostatic acid phosphatase are not secreted by animal prostates, the invention was investigated on human prostate tissues collected after surgery and human prostate cell lines (such as DU-145, LNCaP) in cell culture and after implantation in nude mice. Human prostate tissues were investigated in organ culture and after physical and chemical fixations and implantation in nude mice.

FIG. 1 illustrates the structure of the drug 5-fluoro-2'-deoxyuridine and various derivatives that were evaluated alone and after conjugation with rabbit anti-PSA and anti-PACP-IgGs. The purified immunoglobulin fraction of rabbit anti-sera were obtained from Dako (Dako Corp., Carpinteria, Calif.) and its purity was also evaluated using chemiluminescence immunoassay.

To determine whether the PSA IgG-drug-conjugate could be taken up by human prostate cells, small pieces of human prostates, collected after prostatectomies, were placed in organ culture media containing PSA-IgG conjugated with 5-fluoro-2'-deoxyuridine (5-Fu-2'-d), 5-Fu-2'-d-biotin and/or 5-fluoro-2'-deoxyuridine-5'-monophosphate (5-Fu- 2'-d 5'-mp) for 18 to 72 hours. Presence of drug-immunoconjugate in prostate specimens tissues was evaluated by immunofluorescence, immunoperoxidase, and/or Dako kit localization techniques.

FIG. 2 shows a 225× magnification of randomly selected, small (1 to 2 mm$^2$) human prostate pieces that were incubated for 18 hours at 37° C. and 5% $CO_2$ in RPMI-1640 media without the immunoconjugate. The pieces were washed in phosphate buffer saline (PBS), frozen in liquid nitrogen, embedded in OCT (an embedding media obtained from Lab Tek Producto; Miles Lab. Inc., Naperville, Ill.), sectioned with a cryostat at 5 $\mu$m, fixed in 100% acetone and processed for the reaction products using the Dako kit (Santa Barbara, Calif.). The section does not show any labeling because the PSA-IgG-drug immunoconjugate was not incorporated in prostate tissue.

FIG. 3 shows a 225× magnification of human prostate tissue that was incubated for 18 hours in RPMI-1640 media with an immunoconjugate; namely rabbit anti-PSA IgG-5-FU-2'd-biotin (1:20 dilution). Samples were washed with PBS, frozen in liquid nitrogen, embedded in OCT, sectioned with a cryostat at 5 $\mu$m, fixed with 100% acetone and processed for the localization of immunoconjugate using the Dako kit. The prostatic cells show products of the labeling reaction that are not present in the stromal tissues. Thus, immunostaining shows that the immunoconjugate is specific for the epithelial cells.

Figure 4:

To demonstrate the presence of PSA-IgG conjugated with 5-Fu-2'-d in prostate tumors, portions of prostate pieces were incubated in organ culture media for 18 hours at 4° C., washed with PBS, sectioned with a cryostat, fixed with 100% acetone and incubated with goat anti-rabbit IgG conjugated with fluorescein isothiocyanate (FITC) for 1 hour. Sections were examined for fluorescence using a Zeiss epifluorescence microscope and a Zeiss blue barrier filter. FIG. 4 illustrates (225× magnification) the presence of PSA-IgG-drug-immunoconjugate in epithelial cells of human prostate, but not in the stromal tissues between the glands. Immunofluorescence techniques provided results comparable to those in FIG. 3. These results confirm the specificity of the immunoconjugate for the prostatic epithelial cells.

Figure 5:
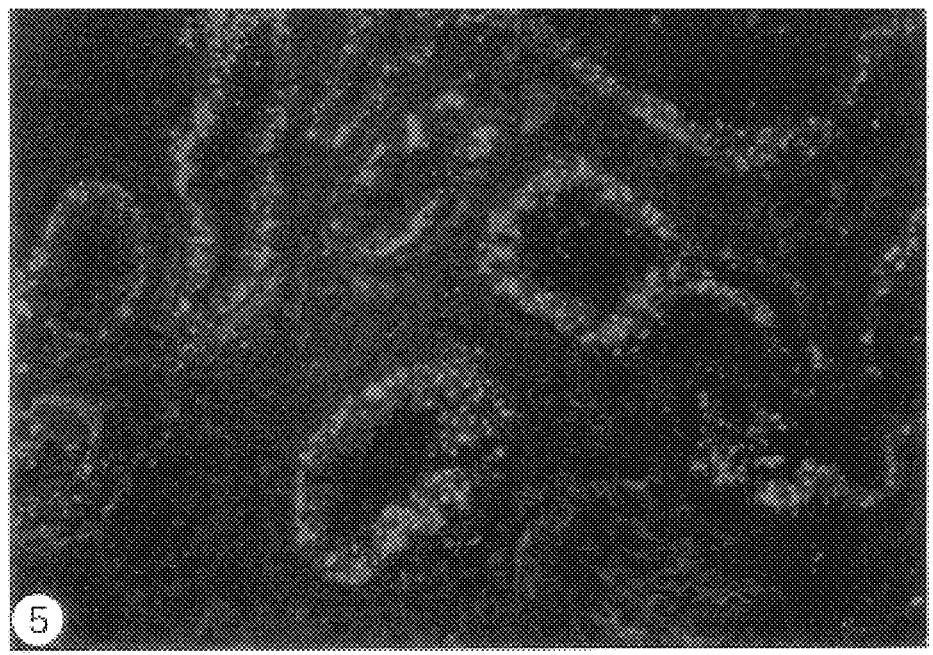

That both PSA-IgG and 5-Fu-2'-d-5'-mp reach the same groups of prostate cells is demonstrated by a double immunofluorescence technique. For this purpose, PSA-IgG was conjugated with rhodamine (which produces red fluorescence) and 5-Fu-2'-d-5'-mp was conjugated with fluorescein isothiocyanate (FITC) (which produces blue fluorescence). These separately labeled products were then conjugated together producing PSA-IgG-rhodamine-5-Fu-2'-d-5'-mp-FITC (PRFF) immunoconjugate. Cryostat sections were then incubated with PRFF for 1 or 18 hours. Human prostate section showing a Gleason histologic score 5 cancerous prostate tumor was examined using a Zeiss epifluorescence microscope and Zeiss green and blue excitation and barrier filters, respectively. FIG. 5 illustrates (225× magnification) that localization of red colored rhodamine occurred in epithelial cells, and not in prostatic stromal tissues which do not produce prostatic specific antigen.

Figure 6:

FIG. 6 shows the result (magnification ×225) when a blue filter was used to visualize the presence of drug in the same group of prostatic tumor cells. In other words, the double immunofluorescence technique showed that the drug was indeed conjugated to PSA-IgG and it reached the target cells, i.e., prostatic epithelial cells.

Figure 7:
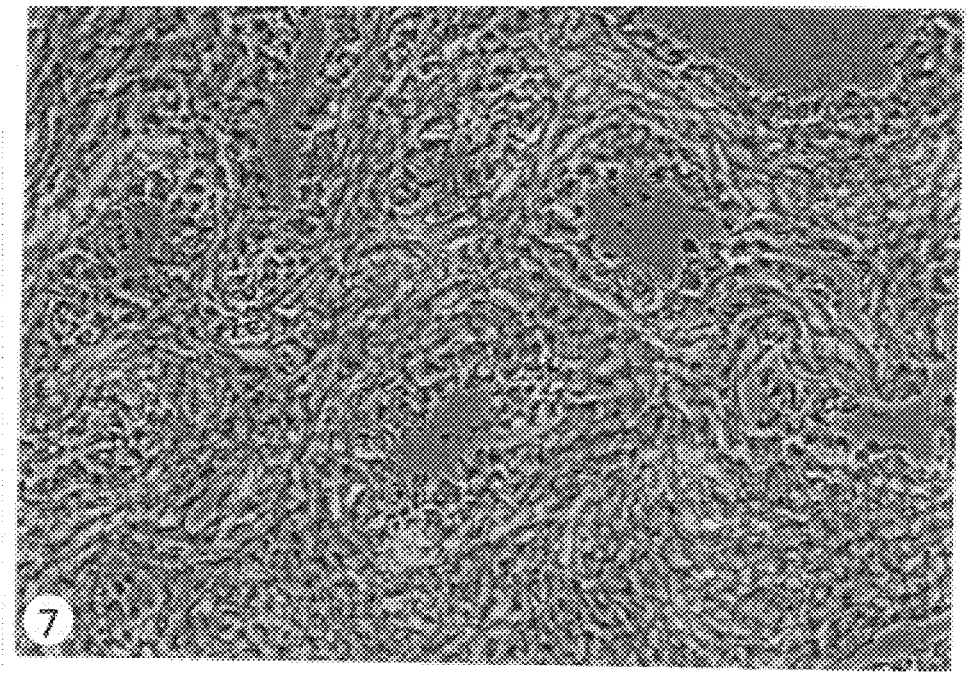

FIG. 7 demonstrates the presence of stromal tissues between prostatic glands shown in FIGS. 5 and 6. The prostate section used for rhodamine and fluorescein localization was photographed with a Zeiss microscope equipped with phase contrast. This micrograph (magnification ×225) demonstrates the presence of stromal cells between prostatic glands, but that localization of the immunoconjugate occurred only in the epithelial cells.

Figure 8:

To demonstrate that rhodamine and FITC-labeled immunoconjugate was specific for human prostatic epithelial cells, human kidney, bladder, and colon cryostat sections were incubated with PRFF immunoconjugate. FIG. 8 (magnification ×225) illustrates the absence of rhodamine or FITC localization in the human kidney. Likewise, bladder and colon sections did not show localization of PRFF immunoconjugate (not illustrated). This study demonstrated that PSA-IgG-drug conjugate targeted only prostatic epithelial cells containing prostatic specific antigen. Since the antigen was not present in kidney, bladder, or colon, no localization occurred.

To demonstrate further that PSA-IgG functions as a carrier protein for 5'-Fu-2'-d, the drug was labeled with FITC alone. The conjugate did not contain PSA-IgG. Human prostate sections were incubated for 18 hours with 5'-Fu-2'-FITC labeled drug and examined with a Zeiss epifluorescence microscope. FIG. 9 (magnification ×225) shows the absence of fluorescence in prostatic epithelial or stromal cells, indicating that the drug alone was not specific for prostate cells and that prostatic specific antigen was needed for carrying and binding the drug to epithelial cells.

Figure 10:
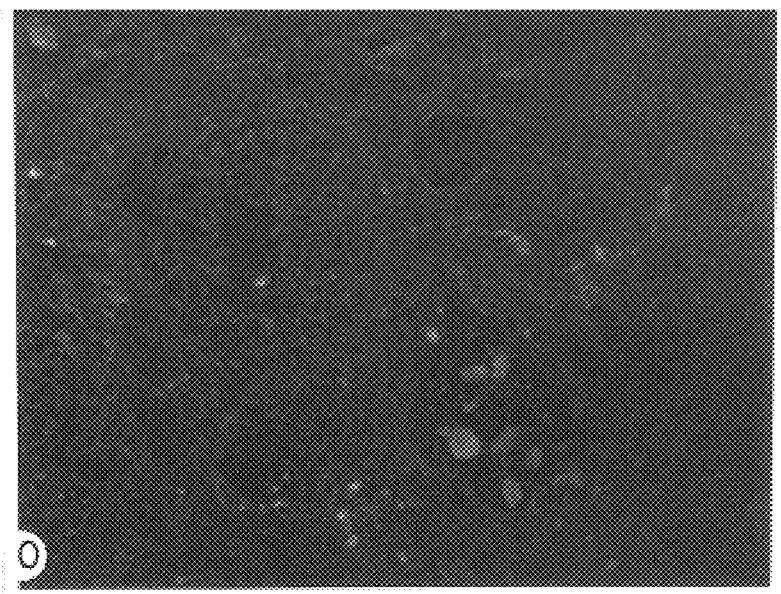

When human prostate sections were incubated with normal rabbit serum without the immunoconjugate PSA-IgG-drug conjugate, followed by treatment with goat anti-rabbit conjugated with FITC, i.e. a negative control experiment, no fluorescence was observed in prostatic epithelial cells, as can be seen in FIG. 10 (magnification ×225), demonstrating the specificity of PSA antibody IgG.

The results shown in FIGS. 2–10 demonstrate that PSA-IgG-drug conjugate binds only to prostatic epithelial cells possessing prostatic specific antigen and it does not bind to any other type of tissues examined. Furthermore, drug alone did not bind to prostatic cells. The negative control experiment demonstrated specificity of the PSA-IgG antibody. Taken together, these figures have shown specificity of PSA-IgG-drug immunoconjugate for neoplastic prostate epithelial cells. Differential immunofluorescence has demonstrated that PSA-IgG functions as a carrier molecule for the chemotherapeutic drug into prostate cells.

The following experiment demonstrates presence of PSA molecules in benign prostatic hyperplasia (BPH).

Figure 11:
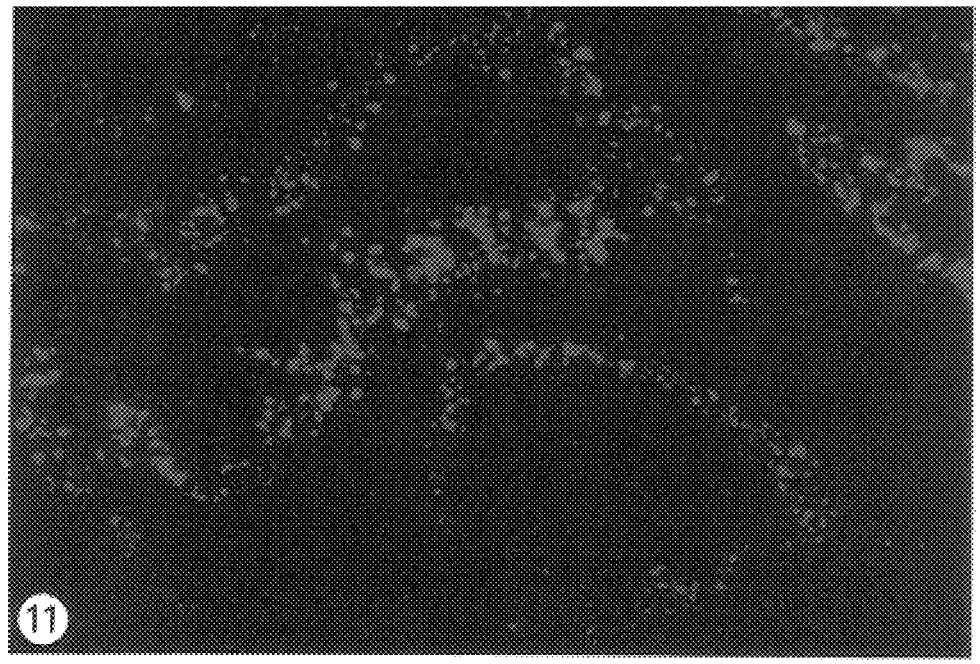
Figure 12:
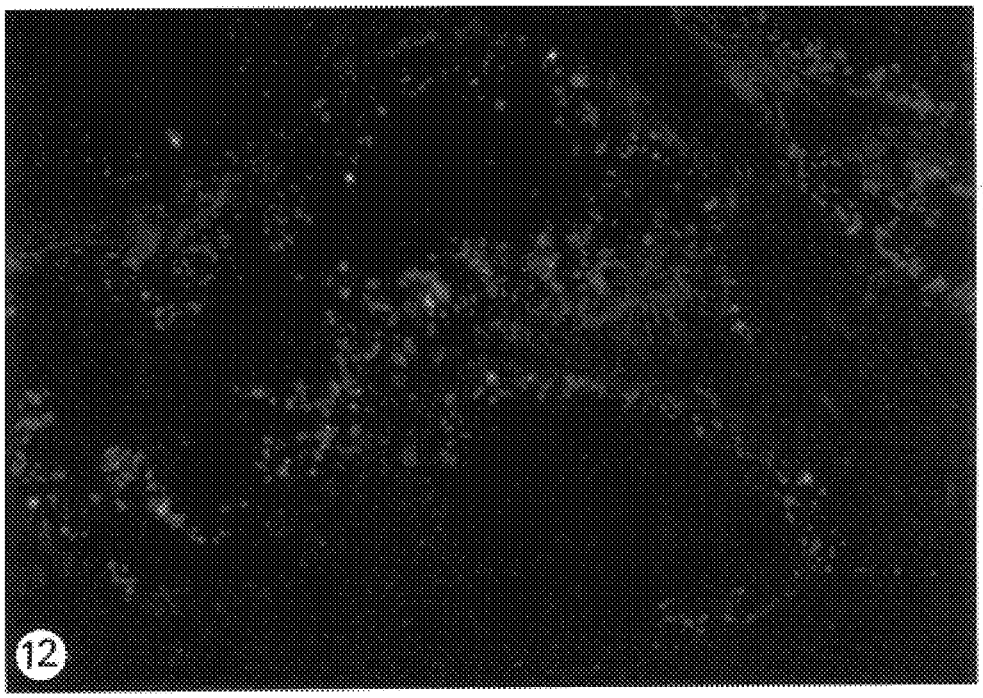

A cryostat section of human benign prostatic hyperplasia was incubated for 18 hours with immunoconjugate PRFF. In this section, the presence of rhodamine in epithelial cells is shown using Zeiss epifluorescence microscope and a red barrier filter. Again, as shown in FIG. 11 (magnification ×225) rhodamine labeling was present only in epithelial cells and not in stromal tissue cells.

Upon analyzing the above section using a blue filter, the observed fluorescence (FIG. 12—225× magnification) demonstrated localization of 5-Fu-2'-d-5'-mp labeled with FITC in the above group of prostatic epithelial cells.

Figure 13:
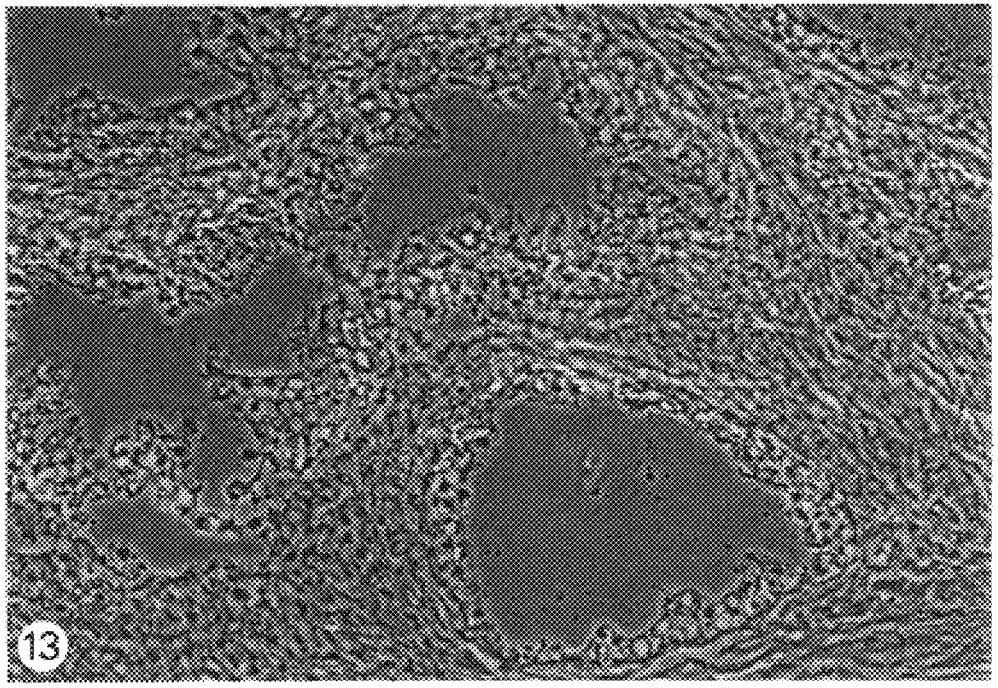

FIG. 13 illustrates the above section as photographed with a Zeiss microscope equipped with phase contrast (magnification ×225). This section shows details of glandular epithelium and stromal tissues shown in FIGS. 11 and 12. This micrograph further demonstrates that both rhodamine and fluorescein labeling occurred only in epithelial cells as expected.

The above shows that PSA-IgG functions as a carrier protein for the conjugated chemotherapeutic agents. The immunoconjugate targeted prostatic epithelial cells and their tumors selectively. Organ culture study showed this immunoconjugate did reach the glandular cells and bound the opithelial cells. Thus, the immunoconjugate is highly specific for prostatic tumors.

In addition to conjugating PSA-IgG with derivatives of 5-fluorouracil, we conjugated anti-human prostatic acid phosphatase IgG with 5-fluoro-2'-deoxy-5'-monophosphate. This resulted in the formation of the immunoconjugate, PAcP-IgG-5-Fu'2'-d-5'-mp. This immunoconjugate, much like the PSA-IgG-drug immunoconjugate, was labeled with a variety of markers (such as rhodamine, fluorescein) and evaluated on human prostate tissue samples obtained after prostatectomy. Human prostatic acid phosphatase is another highly specific marker for human prostate, and the PAcP-IgG-drug immunoconjugate was tested to determine whether the latter immunoconjugate would behave similarly to PSA-IgG-drug immunoconjugate. Much as the PgA-IgG-drug immunoconjugate, the PAcP-IgG-drug immunoconjugate was highly specific for human prostate tumors and it did not bind to epithelial cells of human colon, bladder, kidney, or lung.

In addition, several types of chemotherapeutic agents have been used to treat human prostate and other solid organ tumors (Yogoda, A., and Petrylak, D., Cancer 71: 1098–1109, 1993; Rangel, C., Matzkin, H., and Soloway, M. S., Urology, 39:577–582, 1992; Tritton, T. R., and Yee, G., Sci., 217:248–250, 1982.). Thus, the present invention was applied to another bioactive agent, doxorubicin (an anthracycline). There are numerous derivatives of anthracyclines, some of which are involved in cytotoxicity and DNA synthesis inhibition. Doxorubicin causes cytotoxicity without entering cells (unlike the fluorouracil derivatives) and it also inhibits DNA synthesis and mitosis. Doxorubicin has been used in the treatment of prostate cancer (Yogoda, A., and Petrylak, D., Cancer 71: 1098–109, 1993; Rangel, C., Matzkin, H., and Soloway, M. S., Urology, 39:577–582, 1992). These treatments required utilization of very high dosages of drugs and showed variable results. Doxorubicin alone is not specific for prostate cancer and affects many other organs in patients.

Doxorubicin was conjugated with PSA-IgG and the immunoconjugate PSA-IgG-doxorubicin resulted. We also conjugated doxorubicin alone with fluorescein. Immunoconjugate prepared using PSA-IgG labeled with rhodamine and doxorubicin with fluorescein was also evaluated on human prostate samples. Using single and double conjugated doxorubicin with markers, it was shown that the immunoconjugate was specific for human prostate as it did not localize in human colon, kidney, bladder, and lung. Our study showed that PSA-IgG-doxorubicin immunoconjugate was carried to prostatic epithelial cells only when PSA-IgG molecules were present. The drug alone did not specifically localize in prostatic epithelial cells. This immunoconjugate did not bind to epithelial or stromal cells.

The present immunoconjugates have the major advantages in the treatment of prostatic diseases (such as prostate cancer, BPH, prostatitis) in contrast to unconjugated chemotherapeutic bioactive agents or toxins. Because of the prostate epithelial cell specificity, the immunoconjugates could be the drug of choice for the treatment of prostatic tumors and prostatic tumor metastases. These immunoconjugates could be used in lower therapeutic doses than any conventional treatments currently being used. Furthermore, the immunoconjugate treatment would specifically target prostate tumors cells.

Nude Mice Study

A study was designed to determine the effects of anti-PSA-IgG-drug complex (immunoconjugate) administered into human prostate cell (LNCaP) tumors grown subcutaneously in nude mice. This experiment was designed to study the cytotoxic effects of the IgG-drug conjugate by administering the agent in the MATRIGEL supporting the tumor cells. MATRIGEL is a solubilized tissue basement membrane preparation extracted from the Engelbreth-Holm-Swarm (EHS) mouse tumor, available from Becton-Dickinson (Collaborative Research Inc, Bedford Mass. MATRIGEL is made predominantly of laminin with type IV collagen, heparan sulfate proteoglycans, etc., polymerized under physiological conditions to produce a reconstituted biologically active matrix material that serves as an in vivo attachment matrix which also promotes cell differentiation in normal and transformed cells. Basement membranes are thin extracellular membranes underlying epithelial cells and separation them from connective tissue. Basement membranes (such as MATRIGEL) allow growth and differentiation into specialized tissues and moderate and control cellular behavior. Five groups of mice were evaluated in this study.

Figure 14:
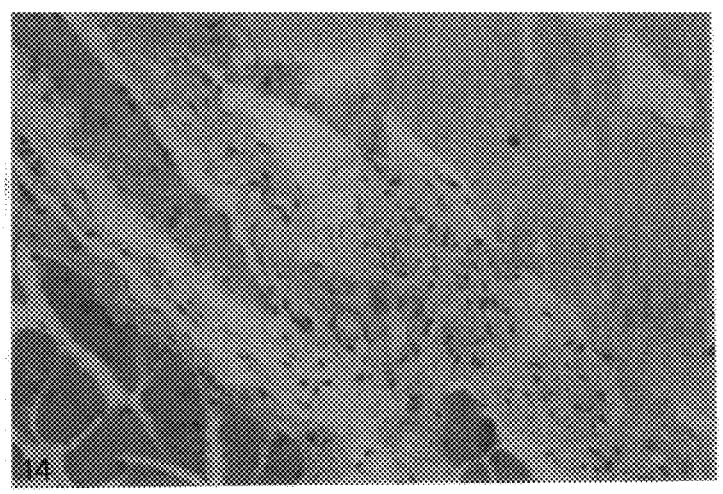
FIGS. 14–18 are micrographs resulting from in vivo experiments with nude mice discussed below.

Group 1. Mice were injected subcutaneously with Matrigel alone (control preparation), no tumor cells and phosphate buffer saline as control media. Analysis of these injection sites revealed that the Matrigel did not contain tumor cells since no tumor cells were injected. The morphology of the Matrigel is illustrated in FIG. 14).

Figure 15:
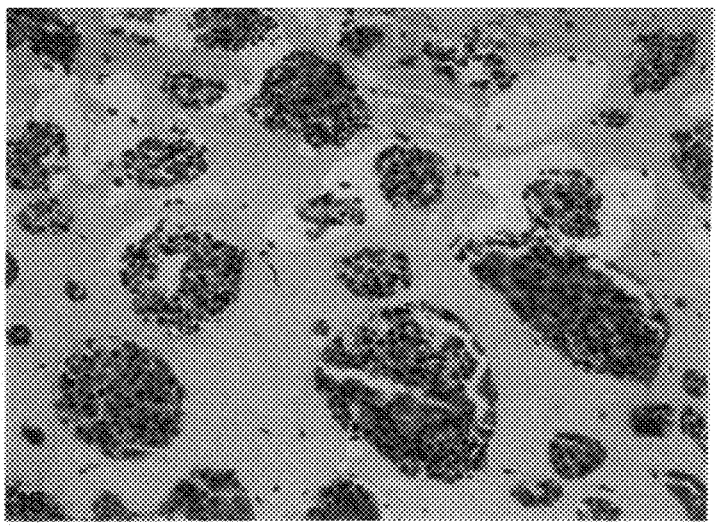

Group 2. Mice were injected subcutaneously with Matrigel containing $10^6$ LNCaP tumor cells and phosphate buffer saline as control media. Analysis of the animals revealed that tumor cells did grow in the Matrigel and formed numerous colonies (FIG. 15).

Figure 16:
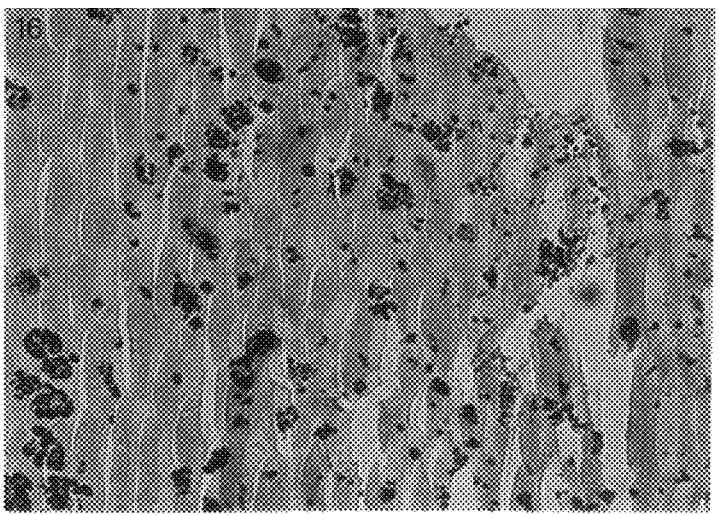

Group 3. Mice were injected subcutaneously with Matrigel containing $10^6$ LNCaP tumor cells with the immunoconjugate and phosphate buffer saline mixed in with Matrigel and cells at the time of injection. Analysis of these mice (FIG. 16) indicated that tumor cells present in the Matrigel were unable to form large colonies in contrast to the colonies shown in FIG. 15.

Figure 17:
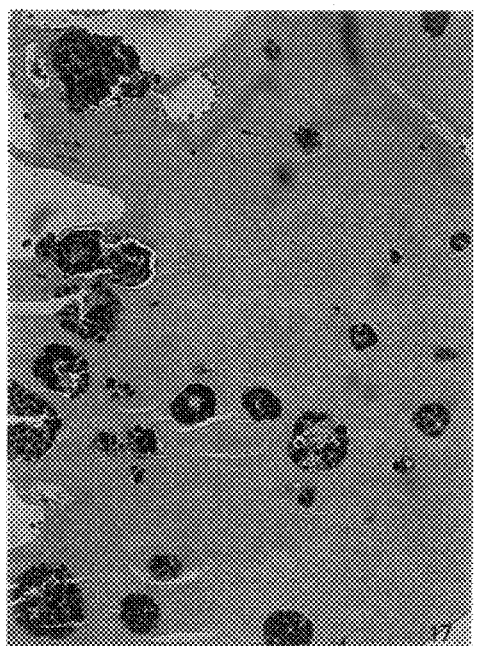

Group 4. Mice were injected subcutaneously with Matrigel containing $10^6$ LNCaP cells and anti-PSA IgG alone (antibody control). Analysis of this group of mice showed that tumor cells formed colonies, but the number of colonies was fewer and smaller than in the Group 2 mice. The pattern of colony formation was similar to those of the Group 2 mice (FIG. 17).

Figure 18:
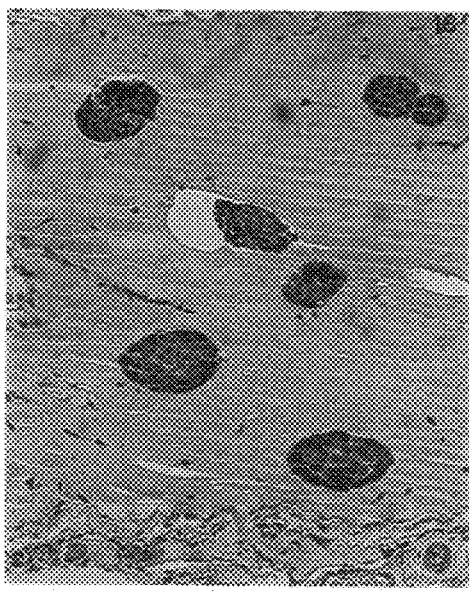

Group 5. Mice were injected subcutaneously with Matrigel containing $10^6$ LNCaP cells. These tumors were allowed to grow for 21 days, at which time they received two sequential injections of anti-PSA IgG-drug conjugate. These mice were followed for changes in tumor size and sacrificed 30 days after the beginning of injection treatments. In the group of mice treated with the immunoconjugate, the number of tumor cell colonies was fewer than in any of the groups evaluated earlier (FIG. 18).

The study on nude mice shows that the immunoconjugate was more effective in reducing the number of tumor colonies than was the antibody alone (group 4). It is interesting to note that very early treatment with the immunoconjugate prevented formation of large colonies. It should be noted that the active agent was administered in Groups 3 and 5 in an amount of about 65 µg/g, suggesting that similar results could be obtained for a range of at least about 50–100 µg/g. Ordinarily, it would be expected that a dosage of about 500 µg/g would be necessary to achieve the results seen in Group 5.

In our study, we found that measuring tumors while still growing in nude mice is not as accurate, especially when tumors were small, as the measurement and weighing them after excision. Since the in situ measurement of tumors was not suitable, we evaluated the immunoconjugate effects on tumors by localization of markers for cell proliferation (such as proliferation cell nuclear antigen:PCNA) and cell death (nuclear DNA fragmentation). Preliminary evaluation of our data indicated that in immunoconjugate treated mice there were fewer proliferating cells than in the untreated mice. Furthermore, the treated tumors showed increased cell death over the untreated group. These two methods could also be evaluated by establishing immunoconjugate treatment for human prostate tumors implanted in nude mice as well as for human prostate tumors in organ culture.

With the advent of newer techniques (such as ultrasonic imaging, PSA in serum), many incidental and early stage prostate cancers are being diagnosed. Some of these tumors develop metastatic disease, while others remain dormant. In some cases, watchful waiting treatment is given while others may receive prostatectomy and/or hormonal treatment. Prostatectomy has high morbidity, altered life style, and even mortality. In the early stage and incidental prostate cancers, the immunoconjugates could be used as well.

For example, early stage tumors, which are often confined to the prostate gland, could be injected with the immunoconjugate. The immunoconjugate would be given in therapeutic dosages and directly into intraprostatic tumor sites via the transurethral route. In this case direct injection may prove to be very effective since it would bind to prostatic epichelial tells tumor, inhibit DNA synthesis, and produce cytotoxic effects. Infusion of the immunoconjugate in the prostate has the advantage of draining the immunoconjugate via prostatic lymphatics and small venules. This drainage system would undoubtedly produce cytotoxic effects on prostate tumor cells if they are present in regional pelvic lymph nodes as well as in the pelvic bone areas.

Another problem with the PSA or PAcP antibody-based immunoconjugate is that of the immunoconjugate binding to serum PSA or PAcP, since these may be increased in cancer or BPH patients. It is possible that substantially higher dosages of immunoconjugates will be required in human patients. However, there are methods available to overcome this drawback. For example:

a) Initially, patients will be treated with humanized, unconjugated antibody which would bind serum PSA (or PAcP) and this could be followed by immunoconjugate treatment. This approach would allow the immunoconjugate to reach the target primary tumor as well as metastatic prostate tumor cells, since the unconjugated antibody would have bound the serum PSA (or PAcP) with the unconjugated, humanized antibody.

b) Another approach to reduce binding of immunoconjugate to serum PSA (or PAcP) would be to treat prostate cancer patients with the current conventional hormone and/or chemotherapeutic treatments for a short period of time. This would reduce serum PSA (or PAcP) to a very low level. The immunoconjugate treatment then could be utilized for targeting prostatic tumor cells. Similar approaches could be used to overcome similar problems in the treatment of other conditions and other tissues and organs.

The invention has been described with reference to various specific and preferred embodiments and techniques. However, it should be understood that many variations and modifications may be made while remaining within the spirit and scope of the invention.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method for delivering a bioactive substance to a prostate gland in an animal, comprising administering to the animal an immunoconjugate which comprises an antibody or antigen-binding fragment thereof for prostate specific antigen linked to a bioactive agent for treating a condition of the prostrate gland.

2. The method of claim 1, wherein the immunoconjugate is administered by injection or delivered directly to the prostate gland.

3. The method of claim 1, wherein said condition is selected from the group consisting of adenocarcinoma of the prostate, benign prostatic hypertrophy and prostatitis.

4. The method of claim 1 wherein the animal is human.

5. The method of claim 1 wherein said condition is a solid tumor and the bioactive agent is useful for treating the cells of the solid tumor.

6. The method of claim 1, wherein the antibody is a polyclonal antibody.

* * * * *